US009649416B2

United States Patent
Goco

(10) Patent No.: US 9,649,416 B2
(45) Date of Patent: May 16, 2017

(54) RETRACTOR SUCTION CATHETER

(71) Applicant: Paulino Edwardo Goco, Murfreesboro, TN (US)

(72) Inventor: Paulino Edwardo Goco, Murfreesboro, TN (US)

( * ) Notice: Subject to any disclaimer, the term of this patent is extended or adjusted under 35 U.S.C. 154(b) by 375 days.

(21) Appl. No.: 14/451,541

(22) Filed: Aug. 5, 2014

(65) Prior Publication Data
US 2016/0038170 A1    Feb. 11, 2016

(51) Int. Cl.
*A61M 1/00* (2006.01)
*A61M 25/00* (2006.01)
(Continued)

(52) U.S. Cl.
CPC ............ *A61M 1/008* (2013.01); *A61B 17/02* (2013.01); *A61M 25/02* (2013.01); *A61B 17/24* (2013.01); *A61B 2217/005* (2013.01); *A61M 25/0041* (2013.01); *A61M 25/04* (2013.01); *A61M 2025/022* (2013.01); *A61M 2025/024* (2013.01);
(Continued)

(58) Field of Classification Search
CPC ............... A61B 17/0218; A61B 17/24; A61B 2217/005; A61B 2218/008; A61M 1/008; A61M 2025/0226; A61M 2025/024; A61M 2210/0618; A61M 2210/065; A61M 25/0041; A61M 25/007; A61M 25/04; A61M 2025/022; A61M 2210/0625; A61M 2210/0656; A61M 2025/0163; A61M 2025/026; A61M 16/0461; A61M 27/00; A61M 1/00; A61M 2210/0643; A61M 25/02; A61M 2025/0286; A61M 2025/0206; A61M 2025/0266; A61M 2025/0273; A61C 17/02; A61C 17/00;
(Continued)

(56) References Cited

U.S. PATENT DOCUMENTS 683,076 A * 9/1901 Simmons ............... A47K 3/287
4/618
759,874 A * 5/1904 Fletcher ................. A47K 3/287
239/567
(Continued)

FOREIGN PATENT DOCUMENTS

DE           9315610 U1 *  2/1994  ........ A61M 16/0461

OTHER PUBLICATIONS

Naraghi, Mohsen, and Arash Kashfi. "Endoscopic resection of nasopharyngeal angiofibromas by combined transnasal and transoral routes." American journal of otolaryngology 24.3 (2003): 149-154.*

(Continued)

*Primary Examiner* — Adam Marcetich
(74) *Attorney, Agent, or Firm* — Dunlap Bennett & Ludwig PLLC

(57) ABSTRACT

A retractor suction catheter used during surgery is provided. The suction catheter may include a tube having an open end and a closed end. The open end may include a fitting. The tube may further include a plurality of openings in between the open end and the closed end. The tube may fit through a subject's oral cavity and out of the mouth. The tube may retract the soft palate so that the surgeon may perform the proper surgery. Further, a vacuum may be attached to the fitting, and therefore fumes and debris may be removed through the apertures.

3 Claims, 2 Drawing Sheets

(51) Int. Cl.
*A61M 25/01* (2006.01)
*A61M 25/02* (2006.01)
*A61B 17/02* (2006.01)
*B08B 15/00* (2006.01)
*A61B 17/24* (2006.01)
*A61M 25/04* (2006.01)

(52) U.S. Cl.
CPC ........... *A61M 2025/0226* (2013.01); *A61M 2210/065* (2013.01); *A61M 2210/0618* (2013.01); *B08B 15/007* (2013.01); *Y10S 128/26* (2013.01); *Y10S 604/902* (2013.01)

(58) Field of Classification Search
CPC ... Y10S 128/26; Y10S 604/902; A47K 3/287; B08B 15/007
See application file for complete search history.

(56) References Cited

U.S. PATENT DOCUMENTS

| | | | | |
|---|---|---|---|---|
| 1,374,430 A | * | 4/1921 | Chevalier | A47K 3/287 4/618 |
| 4,133,315 A | * | 1/1979 | Berman | A61F 5/004 604/909 |
| 4,417,874 A | * | 11/1983 | Andersson | A61C 17/043 433/96 |
| 4,634,425 A | * | 1/1987 | Meer | A61J 15/0003 128/207.18 |
| 4,778,448 A | * | 10/1988 | Meer | A61J 15/0053 128/207.18 |
| 5,279,599 A | * | 1/1994 | Wilk | A61M 1/008 604/313 |
| 5,322,521 A | * | 6/1994 | Wilk | A61M 1/008 433/91 |
| 5,492,538 A | * | 2/1996 | Johlin, Jr. | A61M 25/0068 128/899 |
| 5,941,873 A | * | 8/1999 | Korenfeld | A61B 17/0231 604/313 |
| 2003/0177695 A1 | * | 9/2003 | Manning | A01G 25/02 47/48.5 |
| 2006/0032509 A1 | * | 2/2006 | Milles | A61M 16/009 128/205.12 |
| 2013/0095450 A1 | * | 4/2013 | Ames | A61C 17/043 433/93 |
| 2013/0111811 A1 | * | 5/2013 | Miyauchi | A01G 7/06 47/57.7 |
| 2013/0312768 A1 | * | 11/2013 | Flaherty | A61F 5/566 128/848 |
| 2014/0276653 A1 | * | 9/2014 | Brennan | A61M 27/00 604/540 |

OTHER PUBLICATIONS

Hoffman, Jason, J. Mark Matthews, and Adam R. Reese. "Oral endotracheal tube exchange to the nasal route in a patient with facial trauma." Journal of clinical anesthesia 23.4 (2011): 342.*

* cited by examiner

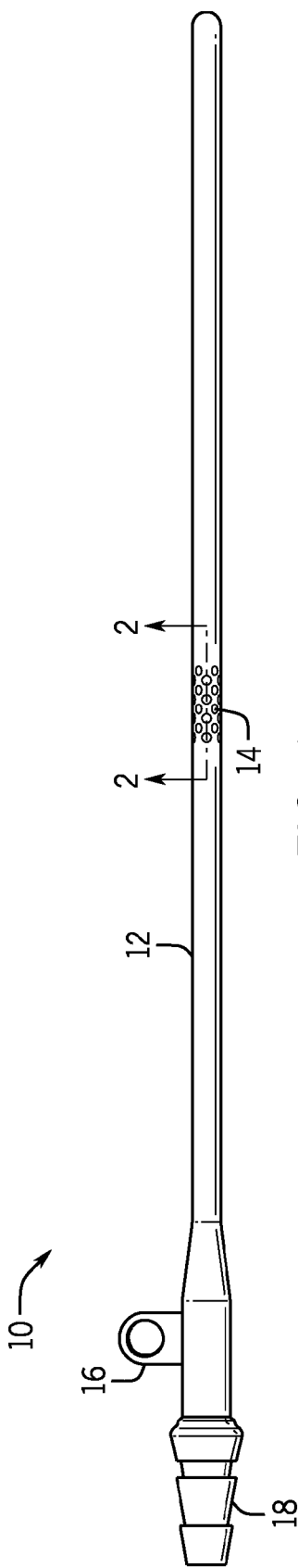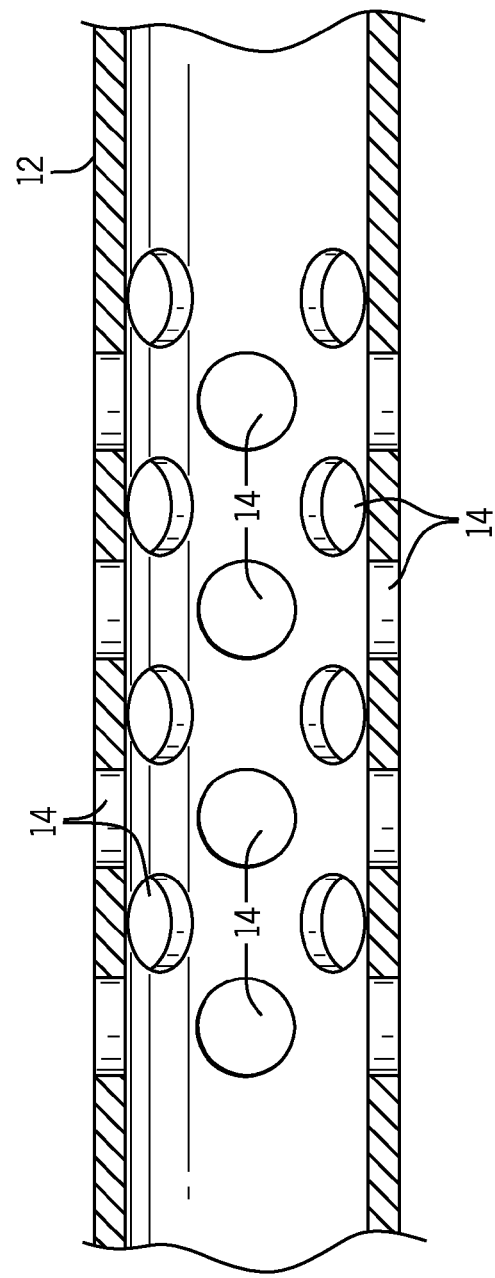

RETRACTOR SUCTION CATHETER

BACKGROUND OF THE INVENTION

The present invention relates to a suction catheter and, more particularly, to a suction catheter that retracts the soft palate.

In medicine, a catheter is a thin tube extruded from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, otolaryngic and ophthalmic applications Catheters can be inserted into a body cavity, duct, or vessel. Functionally, they allow drainage, administration of fluids or gases, access by surgical instruments, and also perform a wide variety of other tasks depending on the type of catheter. The process of inserting a catheter is catheterization. In most uses, catheter is a thin, flexible tube though catheters are available in varying levels of stiffness depending on the application.

When performing procedures on the back of the nose, nasopharynx and/or oral cavity through the mouth, it is necessary to hold back the soft palate to prevent the soft palate from blocking the working area. Further, it is advantageous to remove smoke or vapor produced during the procedure to visualize the surgical site. The current practice during surgeries such as Tonsillectomies and adenoidectomies is to use a small red rubber catheter through the nose and out of the mouth. The catheter is then tied to itself or held with a clamp. Then a second person usually must suction the vapors and/or smoke with a separate suction device interfering with visualization of the operating field. Using two devices in a small operating area is awkward and blocks visualization in the working area.

As can be seen, there is a need for an improved catheter used to perform the surgeries listed above.

SUMMARY OF THE INVENTION

In one aspect of the present invention, a suction catheter comprises: a tube having a first end, a second end, and at least one aperture disposed through the tube in between the first end and the second end, wherein the first end comprises a closed end, and the second end comprises a fitting formed to releasably secure to a vacuum hose, wherein the closed end is formed to fit through the nasal cavity and out of the mouth so that the at least one aperture is located within at least one of the oral cavity and the nasal cavity.

In another aspect of the present invention, a suction catheter comprises: a tube having a first end, a second end, and a plurality of apertures disposed through the tube and near a center point in between the first end and the second end, wherein the first end comprises a closed end, and the second end comprises a fitting formed to releasably secure to a vacuum hose; and an attachment mechanism disposed on the tube near the first end and configured to y secure the tube near the second end.

In another aspect of the present invention, method of treatment comprises: providing a tube comprising a first closed end and a second open end, and at least one aperture disposed through the tube; and inserting the first closed end through the nasal cavity and out of the mouth and thereby retracting the soft palate, wherein the at least one aperture is within at least one of the oral cavity and the nasal cavity.

These and other features, aspects and advantages of the present invention will become better understood with reference to the following drawings, description and claims.

BRIEF DESCRIPTION OF THE DRAWINGS

FIG. 1 is a side elevation view of an embodiment of the present invention demonstrating the present invention in an extended position;

FIG. 2 is a cross-sectional detail view of the apertures taken along line 2-2 of FIG. 1.

DETAILED DESCRIPTION OF THE INVENTION

Figure 3:
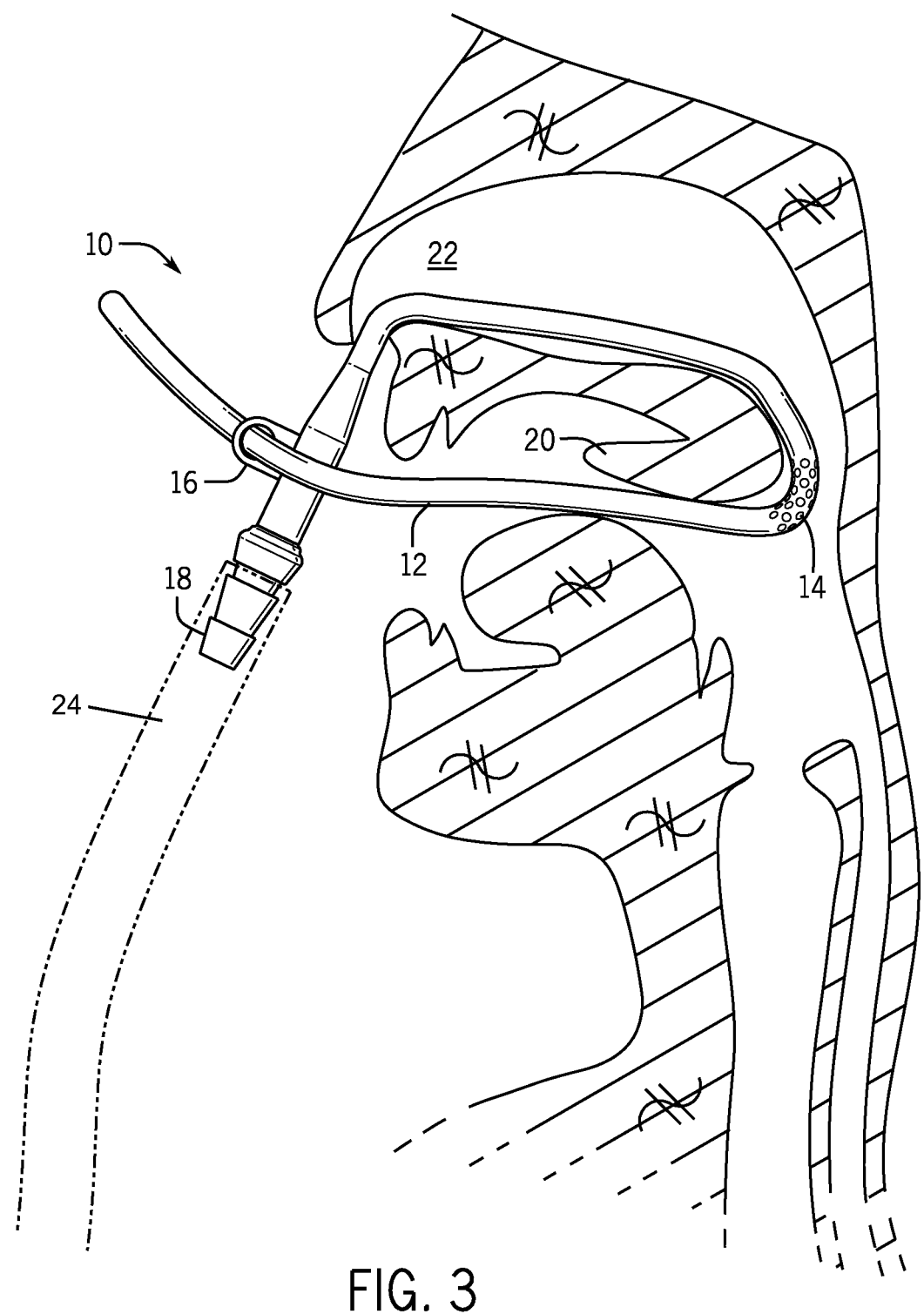
FIG. 3 is a side elevation view of the embodiment of FIG. 1 demonstrating the present invention in use.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a suction catheter used during surgery or other procedures. The suction catheter may include a tube having an open end and a closed end. The open end may include a fitting. The tube may further include a plurality of openings in between the open end and the closed end. The tube may fit through a subject's oral cavity and out of the mouth. The tube may retract the soft palate so that the healthcare provider may perform the proper procedure. Further, a vacuum may be attached to the fitting, and therefore fumes and debris may be removed through the apertures. Further, a light source may be attached or built into the fitting , and therefore allow illumination of the surrounding areas. Further , a camera may be attached or built into the fitting and allow video or photos of the surrounding area.

The present invention includes a flexible non-conductive suction catheter that retracts the soft palate and suctions fumes/smoke. The catheter may hold the soft palate away from the surgical field and also act as a conduit to remove vapors and smoke that is produced during the surgery and also allow irritation of the surgical site. By utilizing one device to hold back soft tissue and provide suction, the present invention provides more room to visualize the procedure and further allows a single person to perform the procedure. The present invention may retract the soft palate and remove vapors/smoke thereby eliminating a separate second suction device used during surgery.

The present invention includes a flexible medical grade soft catheter with an end designed to attach to suction tubing with an opposite blunt end. Under general anesthesia, the blunt end may be inserted into the nose and come out of the mouth. The catheter may then be secured to an attachment on the catheter exiting the nose to hold the soft palate out of the surgical field. The catheter may include a plurality of small holes placed circumferentially around the catheter to allow suctioning of vapor and smoke away from the surgical field. After the surgery is completed the catheter may be removed.

Referring to FIGS. 1 through 3, the present invention includes a suction catheter 10. The suction catheter 10 may include a tube 12 with a first end and a second end. The tube 12 may further include at least one aperture 14 through the tube 10 in between the first end and the second end. In certain embodiments, the first end of the tube 12 may be a closed end i.e. a blunt end, and the second end of the tube may be open and including a fitting 18 formed to releasably secure to a vacuum hose 24.

In certain embodiments, the suction catheter 10 of the present invention may include a reversible attachment mechanism 16. The attachment mechanism 16 may be attached to the tube 12 near the second end, and thereby near the fitting 18. The attachment mechanism 16 may extend from the tube 12 and may releasably attach to the tube 12. For example, the attachment mechanism 16 may releasably attach to the tube 12 near the first end.

In certain embodiments, the attachment mechanism 16 may include any device that may attach a first portion of the tube 12 to a second portion of tube 12. As illustrated in the Figures, the attachment mechanism may include a tab extending from the tube 12. An opening may be disposed through the tab. The tube 12 may be inserted into the opening and thereby secure the tube 12 within. However, the attachment mechanism 16 is not limited to a tab and may include clips, snaps, bands, and the like, so that an opposite end of the tube may releasably attach to the attachment mechanism 16. The attachment of the of tube 12 to itself may pull the soft palate out of the way, as well as consolidate the tube 12 for convenient surgical performance.

In certain embodiments, the at least one aperture 14 may be located near a center point in between the first end and the second end. Therefore the apertures 14 may disposed within at least one of the oral cavity and the nasal cavity 22, such as near the soft palate 20, when inserted into a subject. The at least one apertures 14 may include a plurality of apertures 14 oriented circumferentially around the tube and adjacent to one another. The apertures 14 may vent any smoke, fumes or other debris within the oral or nasal cavity 22.

The present invention may further include a method of treatment using the suction catheter described above. The method of treatment may include providing a tube having a first closed end and a second open end, with at least one aperture disposed through the tube in between the first end and the second end. The tube may be inserted into a subject by inserting the first closed end through the nasal cavity and out of the mouth. The tube may be tightened to retract the soft palate and attached to the mouthgag or the attachment mechanism. The at least one aperture may be within the at least one of the oral cavity and the nasal cavity. For example, the apertures may be located around the soft palate.

The method of the present invention may further include attaching the tube near the first end to the tube near the second end using the attachment component. For example, the first end of the tube may fit through the opening through the tab, thereby securing the first end out of the way of the operation and tightening the tube to retract the soft palate. As mentioned above the second open end may include a fitting. The method of treatment may further include attaching a vacuum tube to the fitting. The vacuum may be turned one so that fumes, smoke and debris within the oral or nasal cavities may be pulled through the at least one aperture.

It should be understood, of course, that the foregoing relates to exemplary embodiments of the invention and that modifications may be made without departing from the spirit and scope of the invention as set forth in the following claims.

What is claimed is:

1. A method of treatment comprising:
providing a tube comprising a first closed end, a second open end comprising a tube fitting and a tab extending from the tube near the second open end, wherein the tab comprises an opening formed therethrough, wherein a plurality of apertures are formed through the tube in between the first end and the second end;
inserting the first closed end through a nasal cavity, through an oral cavity and out of a mouth of a user;
positioning the plurality of apertures in between the oral cavity and the nasal cavity adjacent to a soft palate of the user;
inserting the first closed end through the opening of the tab, thereby attaching the tube to itself; and
retracting the soft palate with the tube.

2. The method of claim 1, further comprising the step of attaching a vacuum hose to the second open end.

3. The method of claim 1, wherein the plurality of apertures are centrally disposed in a cluster between the first closed end and the second open end and are oriented circumferentially around the tube adjacent to one another.

* * * * *